United States Patent
Benveniste et al.

(10) Patent No.: US 9,421,225 B2
(45) Date of Patent: *Aug. 23, 2016

(54) METHOD AND SYSTEM FOR PRODUCING A SUBSTANCE OR A SIGNAL WITH A COAGULATING OR ANTICOAGULANT EFFECT

(75) Inventors: Jacques Benveniste, Paris (FR); Didier Guillonnet, Cagnes-sur-mer (FR)

(73) Assignee: DiGiBio, Paris (FR)

( * ) Notice: Subject to any disclaimer, the term of this patent is extended or adjusted under 35 U.S.C. 154(b) by 1387 days.

This patent is subject to a terminal disclaimer.

(21) Appl. No.: 12/633,271

(22) Filed: Dec. 8, 2009

(65) Prior Publication Data

US 2010/0233296 A1 Sep. 16, 2010

Related U.S. Application Data

(63) Continuation-in-part of application No. 09/787,781, filed as application No. PCT/FR99/02269 on Sep. 23, 1999, now abandoned.

(30) Foreign Application Priority Data

Sep. 23, 1998 (FR) ...................................... 98 12058
Feb. 22, 1999 (FR) ...................................... 99 02329

(51) Int. Cl.
*A61K 33/06* (2006.01)
*A61K 31/727* (2006.01)
(Continued)

(52) U.S. Cl.
CPC ............... *A61K 33/06* (2013.01); *A61K 31/727* (2013.01); *A61K 33/00* (2013.01); *A61K 41/0004* (2013.01); *G01N 33/86* (2013.01); *G01N 37/005* (2013.01)

(58) Field of Classification Search
CPC .............. G01N 33/86; G01N 33/4905; G01N 2015/0092; G01N 33/54326; G01N 2011/0066; G01N 29/02; G01N 33/5438; C12Q 1/56; B01L 2200/0647
See application file for complete search history.

(56) References Cited

U.S. PATENT DOCUMENTS 4,095,168 A 6/1978 Hlavka
5,110,727 A * 5/1992 Oberhardt ....................... 435/13
(Continued)

FOREIGN PATENT DOCUMENTS

DE 44 32 429 3/1996
WO WO 94/17406 8/1994
(Continued)

*Primary Examiner* — Sally Merkling
(74) *Attorney, Agent, or Firm* — Merchant & Gould P.C.

(57) ABSTRACT

The invention concerns a method and a system for producing a signal, in particular an electric signal, or a substance having a coagulating or anticoagulant effect. The method is characterized in that it is based on a source substance with coagulating effect, in particular, $Ca^{++}$ ions, or an anticoagulant affect, in particular heparin. The method consists in: transforming the electromagnetic field derived from said source substance located in the chamber, into a signal, in particular an electric signal, using a transducer-receiver sensing the electromagnetic field; applying to a receiving substance located in the chamber, in particular water or a water-ethanol mixture or homeopathic granules, said signal derived from said transducer-receiver, using a transducer-transmitter. After said treatment, the receiving substance, initially inactive, has a coagulating or anticoagulant effect.

8 Claims, 2 Drawing Sheets

Figure 1:
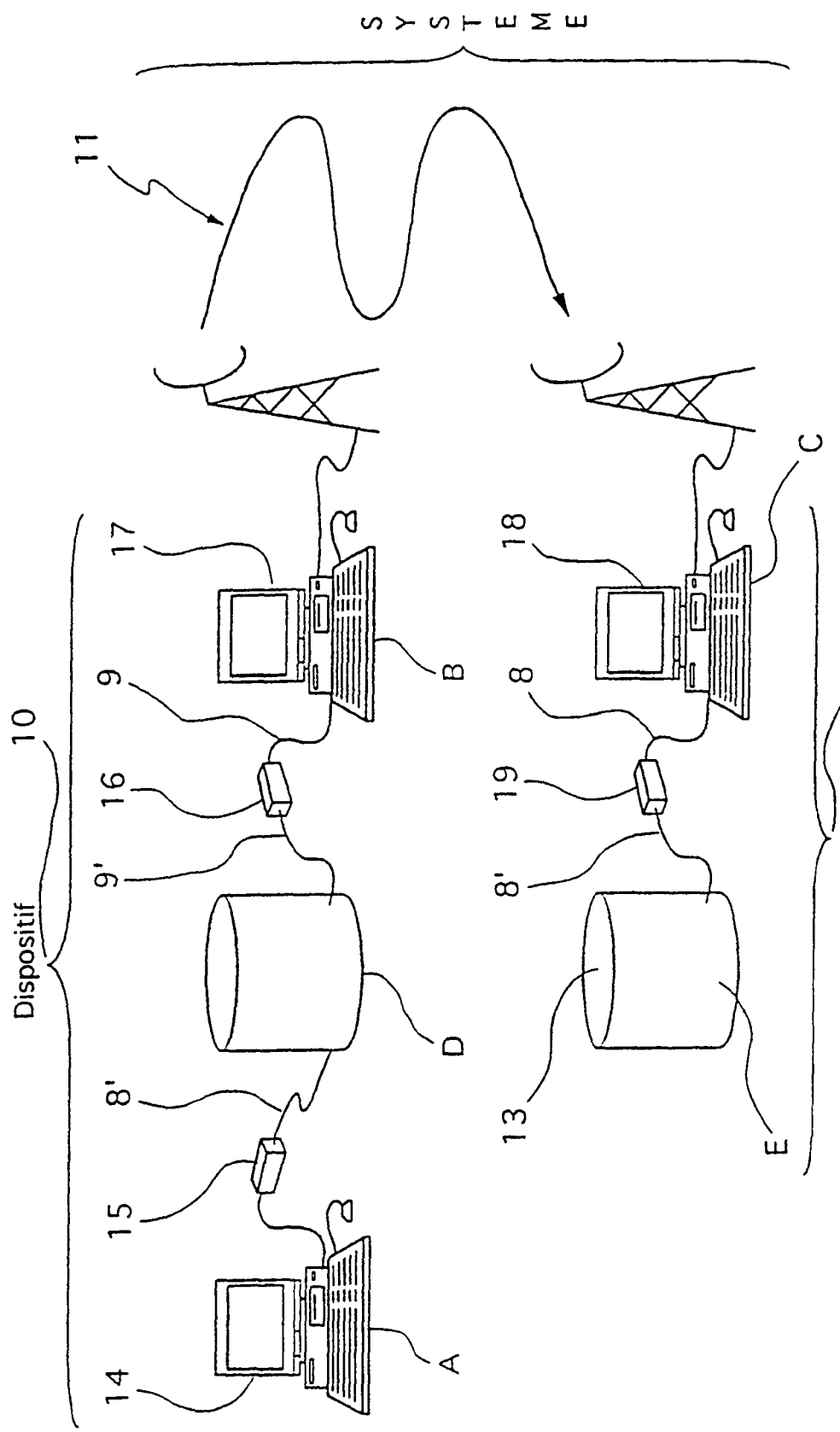

(51) Int. Cl.
  *A61K 33/00* (2006.01)
  *A61K 41/00* (2006.01)
  *G01N 33/86* (2006.01)
  *G01N 37/00* (2006.01)

(56) References Cited

U.S. PATENT DOCUMENTS 5,583,432 A 12/1996 Barnes 5,752,514 A 5/1998 Okamura et al.

FOREIGN PATENT DOCUMENTS

| WO | WO 96/08200 | 3/1996 |
| WO | WO 96/10740 | 4/1996 |
| WO | WO 00/17638 | 3/2000 |

\* cited by examiner

METHOD AND SYSTEM FOR PRODUCING A SUBSTANCE OR A SIGNAL WITH A COAGULATING OR ANTICOAGULANT EFFECT

This application is a Continuation-in-Part of U.S. Ser. No. 09/787,781, filed 24 May 2001, which is a National Stage Application of PCT/FR1999/02269, filed 23 Sep. 1999, which claims benefit of Serial No. 98 120 58, filed 23 Sep. 1998 in France and Serial No. 99 02329, filed 22 Feb. 1999 in France and which applications are incorporated herein by reference. To the extent appropriate, a claim of priority is made to each of the above disclosed applications.

BACKGROUND

The present invention relates to a method and a system for producing a substance or a signal, in particular an electric signal, with a coagulating or anticoagulant effect. The invention also concerns such a substance or such a signal and their therapeutic effects. The invention also relates to a method and a system for testing the coagulating or anticoagulant effect of a substance or a signal.

The present application refers also to WO 00/17638, owned by Digibio, which discloses a system and a device for producing signals from a substance, particularly electric signals characteristic of a biological and/or chemical activity of said substance. WO 00/17638 also discloses the useful means for picking up a signal characteristic of the biological activity of a source substance for being applied to a target substance. After the application of said signal, the target substance, initially inactive, shows unexpectedly a biological activity.

It is known from the research works of Jacques Benveniste, in particular those described in the patent application WO 94/17406 published on 4 Aug. 1994, that one can pick up, from a biological and/or chemical active element such as a chemical compound, a cell or a micro-organism, or from a substance containing this active element, an "electromagnetic signal characteristic of the biological and/or chemical activity or of the biological and/or chemical behaviour" of said substance and/or said active element contained in said substance.

It is also known that it is possible to transform, in particular by means of a transducer, such an electromagnetic signal into electric signals. In the following text one also means by "electric signal characteristic of the biological and/or chemical activity or of the biological and/or chemical behaviour of a substance or of an active element contained in said substance" any electric signal derived by signal digitising and/or processing. In this expression the word "characteristic" is used in the meaning where the physical parameters of the electric signal are specific to the substance or to the active element contained in said substance. In other words, the application of this electric signal, via a transducer, to a biological control system makes it possible:

(i) to induce a biological and/or chemical activity on said biological control system relative to that of the substance of origin or the active element it contains;
(ii) to reveal a characteristic of the substance or the active element it contains, at the origin of said electric signal.

The patent application WO 94/17406 published on 4 Aug. 1994, describes a method and a device for picking up "an electromagnetic signal characteristic of the biological and/or chemical activity or of a biological and/or chemical behaviour" from a biological and/or chemical active element such as a chemical compound, a cell or a micro-organism, or from a substance containing this active element such as a purified preparation, a biological sample, or a living being.

Since then the inventors have discovered that it is possible to improve the quality of the electromagnetic signal picked up as well as the reliability of the method for producing this signal, and that consequently it is possible to produce a characteristic electric signal appropriate for industrial applications. These developments have been described in the French application FR 98 12 058 deposited on 23 Sep. 1998. If need be, the elements of this application, not yet published, and useful for understanding the present invention, will be extracted and inserted in the present application.

SUMMARY

The method of the present invention can employ a device for producing the signal, comprising a chamber, an emitter of the specific excitation field, a transducer-receiver. A characterization is provided for each necessary means, for example, the transducer comprises a bobbin having a soft iron core, an impedance of 300 ohms, an internal diameter of 6 mm, an external diameter of 16 mm and a length of 6 mm. The practical method and the means for recording and treating the signal are disclosed and made explicit in WO 00/17638.

In the present specification also we also describe the means for transmitting the obtained signal in the form of a digital file.

The step of application of the obtained signal to a target biological system, such as water, is also precisely described. Here too, the necessary means are clearly disclosed, for example, the transducer technical characteristics allowing to apply the signal.

The steps, allowing to pick up the electromagnetic signal of a source substance to be applied to a target substance, are those disclosed in WO 94/17406.

The electromagnetic signal characteristic of the substance biological activity shows a frequency in the field of the acoustic frequency. The electric signal at the radiation transducer terminal has amplitude about 2 volt alternating-current, for example, the amplitude is 2 volt alternating-current.

The present application relates also to a method applied to substance showing a biological activity distinct of coagulating or anticoagulating effect, said substance having been obtained from a source substance having said biological effect. After a treatment of the substance, this substance, called "treated substance", do not contains molecules from the source substance in a significant amount. For example, said source substance is heparin.

The above-mentioned treatment comprises the following steps:
  transforming the electromagnetic field coming from said source substance having a biological effect into a signal by means of a transducer-receiver picking up said electromagnetic field,
  applying to a receptor substance, said signal derived from said transducer-receiver, by means of a transducer-transmitter,
  putting the treated substance into a chamber, sheltered from electromagnetic fields.

The invention is based on the fact that specific signals of a substance can be produced by using a electromagnetic frequency spectrum comprised between 20 Hz and 20 kHz, and that water can memorize these electromagnetic signals.
Method and System According to the Invention for Producing a Substance with a Coagulating or Anticoagulant Effect The method according to the invention for producing a substance with a coagulating or anticoagulant effect, from a source substance with a coagulating effect, particularly $Ca^{++}$ ions, or an anticoagulant effect, in particular heparin, comprises at least the following stages.

Stage 1 has the aim of transforming the electromagnetic field from said source substance into a signal, particularly a characteristic electric signal, by means of a transducer-receiver picking up said electromagnetic field.

Stage 2 has the aim of applying to a receptor substance, particularly water or a water-ethanol mixture or homeopathic granules, said signal coming from said transducer-receiver, by means of a transducer-transmitter.

It is to be noted that after the processing defined above, the receptor substance, initially inactive, shows a coagulating or anticoagulant activity. The receptor substance thus treated will hereinafter be called the "treated substance".

The concentration of active elements in the source substance, in particular the concentration of $Ca^{++}$ ions having a coagulating effect or heparin having an anticoagulant effect, can be of the order of 1 µM. It can also be very low and reach $10^{-14}$M. The source substance can also be constituted of homeopathic products, diluted if necessary in water for injectable preparation.

Preferably in order to transform the electromagnetic field derived from said source substance into an electric signal:
    said source substance is placed in a zone submitted to an excitation field of electric, magnetic and/or electromagnetic nature and,
    the resulting fields of interaction between the excitation field and said source substance are transformed into an electric signal, by means of a transducer-receiver picking up said resulting fields.

The system according to the invention for producing a substance with a coagulating or anticoagulant effect, from a source substance with a coagulating effect, in particular $Ca^{++}$ ions, or an anticoagulant effect, in particular heparin, comprises at least the elements defined below.

A transducer-receiver receives the electromagnetic field derived from said source substance. Said transducer-receiver transforms said electromagnetic field into a signal, in particular an electric signal.

A transducer-transmitter makes it possible to apply the signal derived from said transducer-receiver to a receptor substance, in particular water or a water-ethanol mixture or homeopathic granules.

After the processing implemented by the system defined above, the receptor substance, initially inactive, shows a coagulating or anticoagulant activity.

Preferably, the system according to the invention further comprises an emitter generating an excitation field of electric, magnetic and/or electromagnetic nature in the zone where said source substance is situated. A transducer-receiver, receiving the fields resulting from the interaction of said excitation field and said source substance, transforms said resulting field into a signal, in particular an electric signal.

Substance According to the Invention with a Coagulating or Anticoagulant Effect

The invention also relates to a substance with a coagulating or anticoagulant effect. Said substance, in particular water or a water-ethanol mixture or homeopathic granules, is characterised in that it has been processed by means of an electric or electromagnetic signal derived from a source substance with coagulating effects, in particular $Ca^{++}$ ions, or anticoagulant effects, particularly heparin.

The invention also concerns the therapeutic applications of such a substance. The substance according to the invention can be used in the treatment of thromboembolism. It can also be used to carry out scanning tests on coagulation.

Method According to the Invention for Testing the Coagulating or Anticoagulant Effect of a Substance The invention also relates to a method for testing a substance with a coagulating effect, in particular $Ca^{++}$ ions, or an anticoagulant effect, in particular heparin. The method comprises at least the following stages.

Stage 1 has the aim of transforming the electromagnetic field coming from said substance, into a signal, particularly an electric signal, by means of a transducer-receiver picking up said electromagnetic field.

Stage 2 has the aim of applying said signal from said transducer-receiver to a sensitive biological system, directly or indirectly.

Preferably, according to the invention, for transforming the electromagnetic field from said substance into an electric signal:
    said substance is placed in a zone submitted to an excitation field of electric, magnetic and/or electromagnetic nature,
    the fields resulting from the interaction of the excitation field and said source substance are transformed into an electric signal, by means of a transducer-receiver picking up said resulting fields.

Advantageously, the sensitive biological system can be blood or plasma to which said signal is applied by means of a transducer-transmitter. Advantageously, also, plasma rich in platelets can be used.

Advantageously, according to another embodiment variant, the sensitive biological system is an animal, particularly a rabbit, which is administered especially under the tongue, with a substance, particularly water, treated by said signal by means of a transducer-transmitter.

The method according to the invention for testing the coagulating or anticoagulant effect of a substance can be applied to the control of homeopathic products.

Method and System According to the Invention for Producing a Signal with a Coagulating or Anticoagulant Effect The method according to the invention for producing a signal, particularly an electric or electromagnetic signal, having a coagulating or anticoagulant effect, coming from a source substance having a coagulating effect, in particular $Ca^{++}$ ions, or an anticoagulant effect, in particular heparin, comprises at least the stage of transforming the electromagnetic field coming from said source substance into a signal, in particular an electric signal, by means of a transducer-receiver picking up said electromagnetic field.

Preferably, in order to transform the electromagnetic field coming from said source substance into an electric signal:
    said source substance is placed in a zone submitted to an excitation field of electric, magnetic and/or electromagnetic nature,
    the fields resulting from the interaction of the excitation field and the source substance are transformed into a signal, in particular an electric signal, by means of a transducer-receiver picking up said resulting fields.

Preferably, also, the method according to the invention for producing a signal, in particular an electric or electromagnetic signal, having a coagulating or anticoagulant effect, further comprises the stage of controlling the correlations between, on the one hand, the signal derived from said transducer-receiver and, on the other hand, the coagulating or anticoagulant activity of said source substance, by applying, directly or indirectly, said signal to a biological control system and by verifying that said biological control system reacts in conformity with the coagulating or anticoagulant activity of the source substance from which the signal is issued.

Advantageously, the biological control system is blood or plasma to which said signal is applied by means of a transducer-transmitter. Advantageously, one can also use plasma rich in platelets.

Advantageously, in another embodiment variant, the biological control system is an animal, particularly a rabbit, which is administered especially under the tongue, with a substance, particularly water, treated by said signal by means of a transducer-transmitter.

The present invention also relates to a system for producing a signal, in particular an electric or electromagnetic signal, having a coagulating or anticoagulant effect, coming from a source substance with a coagulating effect, particularly $Ca^{++}$ ions, or an anticoagulant effect, in particular heparin. Said system comprises a transducer-receiver receiving the electromagnetic field coming from said source substance, said transducer-receiver transforming said electromagnetic field into a signal, particularly an electric signal.

Preferably, the system according to the invention further comprises an emitter generating an excitation field of electric, magnetic and/or electromagnetic nature in a zone where said source substance is situated. Said transducer-receiver, receiving the fields resulting from the interaction of said excitation field and said source substance, transforms said resulting fields into a signal, in particular an electric signal.

Preferably, also, the system according to the invention further comprises control means for controlling the correlations between, on the one hand, the signal coming from said transducer-receiver and, on the other hand, the coagulating or anticoagulant activity of said source substance. Said control means comprise a transducer-transmitter applying, directly or indirectly, said signal to a biological control system. Said control means further comprise verification means for verifying that the biological control system reacts in conformity with the coagulating or anticoagulant activity of the source substance from which the signal is issued.

Advantageously, the biological control system is blood or plasma to which said signal is applied by means of said transducer-transmitter. Advantageously one can also use plasma rich in platelets.

Advantageously, in another embodiment variant, the control system is an animal, particularly a rabbit, which is administered, especially under the tongue, with a substance, particularly water, treated by said signal by means of a transducer-transmitter.

Signal According to the Invention with a Coagulating or Anticoagulant Effect

The present invention also concerns a signal as such, in particular an electric or electromagnetic signal, having a coagulating or anticoagulant effect. Said signal is obtained from a source substance having a coagulating effect, in particular $Ca^{++}$ ions, or an anticoagulant effect, in particular heparin, by implementing the methods or systems described above. Said signal is characterised in that a biological control system reacts, after direct or indirect application of said signal, in conformity with the coagulating or anticoagulant activity of the source substance from which the signal is issued.

Advantageously, the biological control system is blood or plasma to which said signal is applied by means of said transducer-transmitter. Advantageously one can also use plasma rich in platelets.

Advantageously, in another embodiment variant, the biological control system is an animal, particularly a rabbit, which is administered especially under the tongue, with a substance, particularly water, treated by said signal by means of a transducer-transmitter.

The invention also relates to the therapeutic applications of such a signal. The signal according to the invention can be used, directly or indirectly by the intermediary of a receptor substance, in the treatment of thromboembolism. It can also be used, directly or indirectly by the intermediary of a receptor substance, to carry out scanning tests on coagulation.

Method According to the Invention for Testing the Coagulating or Anticoagulant Effect of a Signal The invention also relates to a method for testing a signal having a coagulating or anticoagulant effect. Said signal is obtained from a source substance having a coagulating effect, in particular $Ca^{++}$ ions, or an anticoagulant effect, in particular heparin, by implementing the methods or systems described above. The method according to the invention comprises the stage of applying said signal, directly or indirectly, to a test biological system and verifying that the test biological system reacts in conformity with the coagulating or anticoagulant activity of the source substance from which the signal is issued.

Advantageously, the test biological system is blood or plasma to which said signal is applied by means of said transducer-transmitter. Advantageously one can also use plasma rich in platelets.

Advantageously, according to another embodiment variant, the test biological system is an animal, particularly a rabbit, which is administered especially under the tongue, with a substance, particularly water, treated by said signal by means of a transducer-transmitter.

The process according to the invention for testing the coagulating or anticoagulant effect of a signal can be applied to production control of homeopathic products.

Figure 1A:
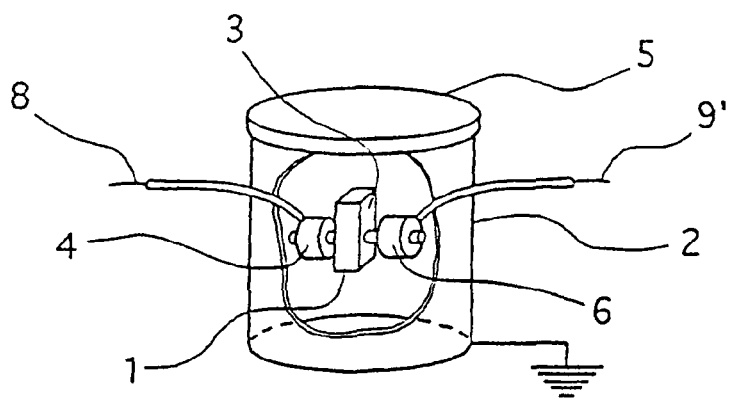
Figure 1B:
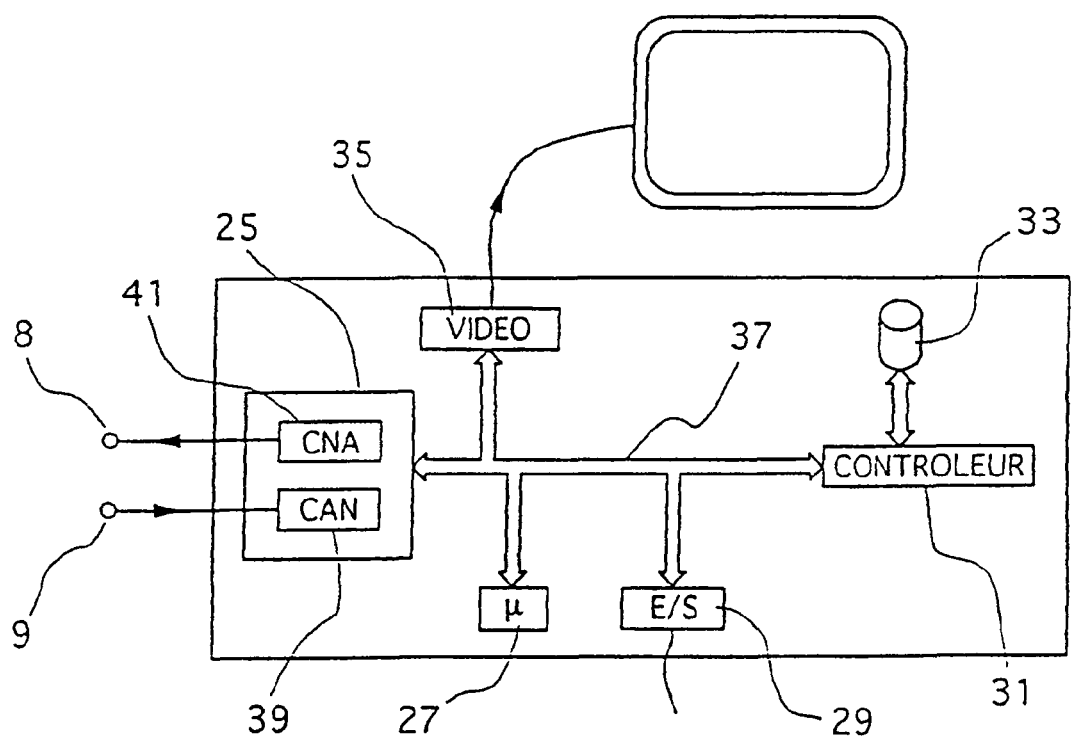
Figure 1C:
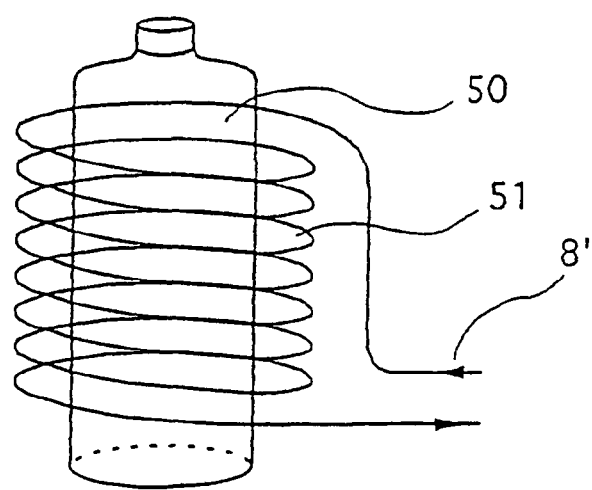

Other characteristics and advantages of the invention will become clear by reading the description of the embodiment variants of the invention, given as an indicatory but non-limiting example, as well as by reading the examples of experiments having made it possible to validate the production method of a substance or a characteristic electric signal, having coagulating or anticoagulant effects. The description refers to the attached drawings in which:

FIG. 1 shows a diagram of an example of an embodiment of a system making it possible to produce a characteristic electric signal, and to apply the characteristic electric signal thus produced to a receptor substance or to a biological control system or to a sensitive biological system, FIG. 1a shows a detailed view in perspective of a part of the production device for the electric signal, showing the excitation field emitter and the transducer-receiver receiving the resulting fields, FIG. 1b shows diagrammatically the type of microcomputer used either for generating the excitation fields, or for recording and transmitting under digitised form the characteristic electric signal, FIG. 1c shows a detailed view in perspective of a part of a transducer-transmitter intended to apply the characteristic electric signal to a receptor substance or to a biological control system or to a sensitive biological system.

GENERAL DIAGRAM OF THE SYSTEM

With reference to FIGS. 1, 1a, 1b and 1c, an example of a system will be described making it possible:

(i) to produce from $Ca^{++}$ ions a characteristic electric signal with a coagulating effect, or from heparin a characteristic electric signal with an anticoagulant effect and (ii) to apply such a characteristic signal to a receptor substance or to a biological control system or to a sensitive biological system.

The system comprises a device 10 for producing a characteristic electric signal of the biological and/or chemical activity or the biological and/or chemical behaviour of a substance 1 or an active element contained in said substance. In the case of the variant described with reference to FIGS. 1, 1a, 1b and 1c, said substance 1 is:

either $Ca^{++}$ ions in solution at 1 µM in water for injectable preparation (e.g. of the Biosédra brand), or heparin at the concentration of 2.5 IU/ml in the same quality of water.

The device 10, located in Paris, for example, produces a characteristic electric signal which is digitised after analog-digital conversion. The signal thus digitised is, in a known manner, transmitted remotely, for example by a computer communication network of the Internet type using radio links 11. The digitised signal thus transmitted is received by an applicator 12, located in New York for example, comprising emission means 13. The emission means 13 make it possible to apply the characteristic signal (after digital-analog conversion) to a receptor substance or to a biological control system or to a sensitive biological system.

The means envisaged for digitising and transmitting remotely the signal characteristic of the $Ca^{++}$ ion or heparin are not indispensable to the embodiment of the invention. They have been described to emphasise the technical and commercial advantages linked to the possibility of producing a characteristic electric signal of the $Ca^{++}$ ion or heparin having, like the source substances from which they are issued, coagulating and anticoagulant effects.

In the case of the variant described with reference to FIGS. 1, 1a, 1b and 1c, the receptor substance is water or a water-ethanol mixture or homeopathic granules, the biological control system or the sensitive biological system is blood or plasma.

I The Device for Producing the Signal Characteristic of the Ca++ Ion or of Heparin The Chamber The device for producing the signal 10 comprises a chamber D, 2 provided with electric and magnetic shielding isolating it from parasitic fields from the environment. The shielded cylindrical chamber is composed of three superposed layers: copper, soft iron, permalloy, made from sheets 1 mm thick. The chamber has an internal diameter of 65 mm, and a height of 100 mm. The chamber is closed by a shielded lid 5. In the chamber 2 is placed a glass container 3 with the dimensions 10 mm×10 mm×45 mm. This container 3 holds 1 ml of the substance 1. That is to say:

either $Ca^{++}$ ions in solution at 1 µM in water for injectable preparation (e.g. of the Biosédra brand), or heparin at the concentration of 2.5 IU/ml in the same quality of water.

The Emitter of the Specific Excitation Field

The emitter 4 is situated inside the chamber. It generates a specific excitation field of an electromagnetic nature. The emitter is supplied by a generator 14. The emitter 4 comprises a bobbin advantageously completed by a magnetic core in soft iron. The emitter bobbin 4 has an impedance of 300 ohms, an internal diameter of 6 mm, an external diameter of 16 mm, and a length of 6 mm. The magnetic core in soft iron is placed in contact with the external walls of the container 3. Said substance 1 is thus submitted to an excitation field emitted by the emitter 4. The generator 14 is designed to generate a low frequency signal especially square or sinusoidal low frequency signals, of pink noise or, advantageously, white noise. The spectrum of the excitation signal supplying the emitter bobbin 4 corresponds closely to the spectrum of audible frequencies (20 Hz-20,000 Hz). The generator 14 can be a generator of an analog signal of known type, using for example a read-only memory (ROM, PROM, EPROM, EEPROM) containing the digital signal of the desired noise. This memory is linked in a known way to a digital-analog converter. A microcomputer 14 can also be used, provided with a sound card 25 comprising a digital-analog converter 41. For example, one can use a computer 14 of the PC type, operating under the WINDOWS® 95 operating system from MICROSOFT and comprising, apart from the sound card 25 a microprocessor 27, an input/output interface 29, a controller 31 for mass storage 33 and a video interface 35 linked by one or several bus 37. The digital-analog converter 41 of the sound card 25 comprises an output terminal 8. The output terminal 8 of the sound card of the microcomputer 14 is linked to the input terminal 8' of the emitter 4, via an amplifier 15 whose specifications are the following: passband from 10 Hz to 20 kHz, gain 1 to 10, input sensitivity +/−1 V. Among the sound cards 25 which can be used, one can cite, for example the Soundblaster 16 card sold by the CREATIVE LABS Company.

The Transducer-receiver

The transducer-receiver 6, situated inside the chamber 2, receives the fields resulting from the interaction between said specific excitation field and said substance 1. The transducer-receiver 6 transforms said resulting fields into an electric signal. This electric signal arrives at the output terminals 9' of the transducer-receiver 6 under the form of a variable difference of potential or of an electric current of variable intensity. The transducer-receiver 6 comprises a bobbin with a soft iron core. This bobbin has an impedance of 300 ohms, an internal diameter of 6 mm, an external diameter of 16 mm, and a length of 6 mm. The magnetic core in soft iron is placed in contact with the external walls of the container 3.

Advantageously, the characteristic electric signal available at the output from the transducer-receiver 6 is amplified by an amplifier-preamplifier 16. The amplifier-preamplifier 16 has the following specifications: passband from 10 Hz to 20 kHz, gain 10 to 100 for an input sensitivity of +/−100 mV.

In the case of the embodiment variant described with reference to FIGS. 1, 1a, 1b, 1c, an emitter 4 of an excitation field is envisaged. The use of such an emitter 4 is favourable for the production of a characteristic electric signal of the $Ca^{++}$ ion or heparin. Nonetheless, one can also pick up, by means of a transducer-receiver 6, a characteristic signal of the $Ca^{++}$ ion or heparin, without implementing an excitation field and without using the shielded chamber.

Recording of the Characteristic Electric Signal

Analog Recording

The recording of the characteristic electric signal, or that of the electric signal derived after amplification or processing, can be carried out in analog by a signal recorder, in particular on magnetic tape, adapted to the frequencies of the characteristic electric signal at the output from the transducer-receiver 6. Since the passband used corresponds to the audio band, one can in particular use a tape recorder. The output terminal 9' of the transducer-receiver 6 is linked to the microphone input or to the line input of such a tape recorder. During play, the characteristic electric signal recorded is collected at an output terminal, in particular at the line output or at the loudspeaker output of the tape recorder.

Digital Recording

Preferably, digital recording of the characteristic electric signal is carried out after analog-digital conversion of the said signal. In order to do this, a microcomputer 17 is used, provided with a signal acquisition card 25. The microcomputer 17 further comprises a microprocessor 27, an input/output interface 29, a controller 31 for mass storage 33 and a video interface linked by one or several bus 37. For example, one can use a PC 17 type computer, operating on the WINDOWS®95 operating system from MICROSOFT. This microcomputer can be of the same type as that used to generate the excitation field. It can be the same microcomputer. The output 9' of the transducer-receiver 6 or the amplifier-preamplifier 16 is connected to the input 9 of the analog-digital converter 39 of the card 25 of the computer 17. Preferably, the analog-digital converter 39 has a resolution higher than 12 bits, and advantageously equal to 16 bits. Preferably, as well, the analog-digital converter 39 has a sampling frequency double the maximum frequency one wishes to be able to digitise, for example 44 kHz. One proceeds with acquisition of a characteristic electric signal for a length of time for example comprised between 1 and 60 seconds (for example 6 sec) and one saves the digital file in the mass storage 33, for example under the form of a sound file with the WAV format.

All links are made of shielded cable. All the apparatus is earthed.

Processing of the Characteristic Electric Signal

Advantageously, in order to process the characteristic electric signal or the derived signal, one uses the Matlab software from the company "The MathWorks".

The digital file, recorded as described above, can if needed undergo digital processing, as for example digital amplification for calibrating the signal level, filtering for eliminating unwanted frequencies, or be transformed into its spectrum by a discrete FOURIER transform, preferably by the algorithm of FFT "Fast Fourier Transform". The time length of the signal produced can be increased by repeating several times in a file a fragment or the totality of the sound file originally produced.

These processing means of the characteristic electric signal can be used to improve performances of said characteristic electric signal. In the case of a first embodiment variant, a second transducer-receiver of the same type as that described above is envisaged. In the absence of said substance, this second transducer-receiver transforms the excitation field into an electric signal. This electric signal is subtracted by an opposition series connection to the signal derived from the first transducer-receiver. Thus one obtains a signal more representative of the interaction between the specific excitation field and the substance.

In the case of a second embodiment variant, the processing means take into account the characteristics of the specific excitation field and reprocess the characteristic electric signal in the following way. First of all one proceeds by calculating the spread of the power spectral density (PSD). Then this power spectral density is contracted by conserving only the frequency band ranging for example from 140 Hz to 14 kHz, and reconstituting a signal from this PSD and neutral phases, generated randomly for example, and finally calibrating the power of the signal thus produced. By neutral phases, one means phases not coming from a source substance presenting a biological activity.

In the case of the embodiment variant described with reference to FIGS. 1, 1a, 1b, 1c, it is envisaged that the characteristic electric signal will be digitised, recorded and processed before applying it to a receptor substance or a biological control system or to a sensitive biological system. These operations are not indispensable for the exploitation of the characteristic electric signal of the $Ca^{++}$ ion or heparin, even though they are favourable for the operation.

The characteristic electric signal available at the transducer-receiver 6 output and, if applicable, from the preamplifier 16 already in itself constitutes a product with possibilities for industrial applications. It will be made clear below for which applications it can be implemented in particular by means of an applicator 12 making it possible to apply them to a receptor substance or a biological control system or a sensitive biological system.

II Remote Transmission of the Characteristic Electric Signal

The file of the characteristic electric signal of the $Ca^{++}$ ion or heparin, recorded under digital form as has just been described, possibly after processing, can be transferred remotely by a computer communication network. This network can comprise radio links 11. The file of the characteristic electric signal of the $Ca^{++}$ ion or heparin thus transmitted, is saved by the mass storage of a microcomputer 18. For example, one can use a computer of the PC type, operating on a WINDOWS®95 operating system from MICROSOFT. This microcomputer 18 can be of the same type as that used for generating the excitation field. The file of the digitised characteristic electric signal thus recorded by the remote microcomputer 18 can be exploited, in known ways, to produce an analog characteristic electric signal. The possibly processed file is transformed by a digital-analog converter 41 of the card 25 (or a separate card) of the computer 18. The digital-analog converter 41 delivers an analog electric signal to its output 8 characteristic of the biological activity of the $Ca^{++}$ ion or the heparin from which it is issued. This analog electric signal can be transformed, as described below, into an electromagnetic field and applied to a receptor substance or a biological control system or to a sensitive biological system.

III The Applicator of the Characteristic Signal of the $Ca^{++}$ Ion or Heparin

With reference to FIG. 1c, an embodiment variant is described below of a system making it possible to apply the characteristic electric signal of the $Ca^{++}$ ion or of heparin to a receptor biological system and to modify its chemical behaviour.

The container 50 holds the biological receptor system. In the case of the embodiment described with reference to FIGS. 1, 1a, 1b, and 1c, the container 50 holds:
- a receptor substance such as water or a water-ethanol mixture or homeopathic granules, or
- a biological control substance or a sensitive biological system such as blood or plasma.

This container 50 is set in an electromagnetic field radiated by a transducer-transmitter 51, typically a bobbin. The bobbin, for example, has a length of 80 mm, an internal diameter of 50 mm, an external diameter of 55 mm, 300 turns of wire of 0.5 mm diameter and an impedance of 4 Ohms. The bobbin 51 is earthed. Without this representing any limiting character whatsoever, the bobbin 51 of the transducer-transmitter has a vertical axis making it possible to introduce the container 50 holding the receptor biological system. The input terminals 8' of this bobbin 51 are linked, in the case of the embodiment variant described, to the output 8 of the digital-analog converter 41 of the microcomputer 18 via an amplifier 19 with the following specifications: passband from 10 Hz to 20 kHz, gain 1 to 20, input sensitivity 250 mV, output power RMS 60 W under 8 ohms, signal to noise ratio 80 dB. The voltage at the terminals of the bobbin 51 has an amplitude of 10 Veff and the signal is applied for 10 minutes. The input terminals 8' of the applicator can also be, in the case of certain embodiment variants, directly connected to the output of the preamplifier 16 or to the output 8 of the digital-analog converter 41 of the computer 17.

Experiments

As an illustration of an embodiment variant,
- a method and a system according to the invention for producing a substance with a coagulating or anticoagulant effect,
- a substance according to the invention having a coagulating or anticoagulant effect,
- a method according to the invention for testing the coagulating or anticoagulant effect of a substance and its application to the production of homeopathic products,
- a method and a system according to the invention for producing a signal with a coagulating or anticoagulant effect,
- a method according to the invention for testing the coagulating/anticoagulant effect of a signal and its application to the production of homeopathic products, the following experiments were carried out.

Effects of Heparin and $Ca^{++}$ Ions on the Coagulation of Human or Rabbit Plasma Heparin (25,000 IU/5 ml, Laboratoire Choay, Sanofi Winthrop) is an anticoagulant acting by inhibiting the transformation of prothrombin into thrombin. The effect of heparin, at the site concerned, is immediate. It acts though the intermediary of a natural inhibitor called a cofactor, or antithrombin III.

Protamine sulphate (10,000 IU/10 ml, Laboratoire Choay, Sanofi Winthrop) forms a salt with heparin and brings about a unit for unit suppression of the latter's anticoagulant effect. 1 ml of protamine solution neutralises the anticoagulant activity of 1000 units of heparin.

The $Ca^{++}$ calcium ion is an ion indispensable for coagulation.

Source Substances and Materials Used

The characteristic electric signals were recorded from samples of 1 ml of the following solutions:
- $Ca^{++}$ in a 1 µM solution in water for injectable preparation (for example the Biosédra brand),
- $Mg^{++}$ in a 1 µM solution in the same quality of water,
- heparin in solution at a concentration of 2.5 IU/ml in the same quality of water,
- heparin+protamine complex (respectively 2.5 IU/ml and 0.025 mg/ml), in solution in the same quality of water.

The material used is described with reference to FIGS. 1*a*, 1*b*, 1*c*. The transducer-receiver 6 has the specifications as described. The transducer-transmitter 51, making it possible to apply the characteristic electric signal to a receptor substance or a biological control system or a sensitive biological system, is an electromagnetic bobbin with the following specifications:
- length: 80 mm,
- internal diameter: 50 mm,
- number of turns: 300 turns,
- impedance: 4 Ohms.

A coagulation evaluation was made using the following rating:
- high coagulation: 2
- moderate coagulation: 1
- no coagulation: 0

Protocol No. 1. "In Vitro" Experiment: Coagulating or Anticoagulant Action of Characteristic Electric Signals on Plasma Rich in Platelets (PRP)

This protocol has the aim of demonstrating that:
- on the one hand, the method and system described make it possible to produce a characteristic electric signal for the $Ca^{++}$ ion and for heparin having respectively a coagulating or anticoagulant effect, and
- on the other hand, the method and system described make it possible to test an electric signal having respectively a coagulating or anticoagulant effect.

As biological control system making it possible to reveal the characteristic electric signal of the $Ca^{++}$ ion and that of heparin, or as sensitive biological system making it possible to test the coagulating or anticoagulant effect of an electric signal, rabbit (or human) plasma is used.

Blood from a "New-Zealand White" rabbit was taken from the artery of the ear and collected on an anticoagulant ACD (9 vol. blood/1 vol. ACD) with the following composition: citric acid 0.8%, sodium citrate 2.2%, anhydrous glucose 2.23%.

After centrifuging (180 gm, 15 minutes) at ambient temperature, the blood separated into 3 layers: from top to bottom, the Plasma Rich in Platelets (PRP), the leukocyte layer and the sediment of red blood cells. The PRP is sampled by pipette by gentle aspiration.

Anticoagulant Effect of a Signal, Anticoagulant Effect of the Characteristic Electric Signal of Heparin 5 ml of PRP are placed in a tube 50 at the centre of an electromagnetic bobbin 51 to be exposed to the signal applied for 10 minutes with a voltage of 10V at the bobbin terminals.

Samples of 1 ml of PRP thus treated are placed in four tubes. Each tube is delivered with 20 µl of $Ca^{++}$ (50, 100, 150 and 200 mM) to obtain final concentrations of calcium in the PRP (of 1,2,3 and 4 mM). They are then left to incubate for 15 to 20 minutes.

The results obtained are presented in the table below:

| | Coagulation evaluation after 20 min | | |
|---|---|---|---|
| Concentration in $Ca^{++}$ (mM) | Without Signal application Av. ± 1SD(n) | Heparin Signal Av. ± 1SD(n) | Heparin + Protamine Complex Signal Av. ± 1SD(n) |
| 1 | 0.00 ± 0.00(5) | 0.18 ± 0.50(22) | 0.42 ± 0.74(21) |
| 2 | 0.75 ± 0.88(8) | 0.25 ± 0.53(24) | 1.25 ± 0.94(24) |
| 3 | 1.75 ± 0.70(8) | 0.54 ± 0.65(24) | 1.91 ± 0.40(24) |
| 4 | 1.75 ± 0.70(8) | 1.41 ± 0.88(24) | 1.91 ± 0.40(24) | n: number of values; Av: average; SD standard deviation

It can be seen that application of a heparin signal has an inhibiting effect on the coagulation of PRP. In the same conditions, the PRP non-exposed to a signal or the PRP exposed to a control signal, for example that of the heparin+ protamine complex, has no inhibiting effect. This coagulation inhibiting effect is especially noticeable for a concentration in $Ca^{++}$ comprised between 2 and 3 mM.

Thus, the biological control system constituted by plasma rich in platelets makes it possible to verify that the characteristic signal of heparin has an anticoagulant effect.

Thus, the sensitive biological system constituted by plasma rich in platelets makes it possible to test whether a characteristic signal has an anticoagulant effect.

Coagulating Effect of a Signal, Coagulating Effect of a Characteristic Electric Signal of the Calcium Ion ($Ca^{++}$)

1 ml of PRP is placed in a tube at the centre of an electromagnetic bobbin to be exposed to the signal applied for 10 minutes with a voltage of 10 V at the bobbin terminals.

The results obtained are presented in the table below:

|  | Without Signal application Av. ± 1SD(n) | Signal Calcium Ca$^{++}$ Av. ± 1SD(n) | Signal Magnesium Mg$^{++}$ Av. ± 1SD(n) |
|---|---|---|---|
| Coagulation evaluation after 60 min | 0.00 ± 0.00 (7) | 1.57 ± 0.75 (14) | 0.00 ± 0.00 (14) |
| Average retraction time | no retraction observed after 24 hr (7) | <12 hr (14) | no retraction observed after 24 hr (14) |

Interpretation

It can be seen that application of a calcium Ca$^{++}$ signal has a PRP coagulating effect comparable to that of calcium Ca$^{++}$ itself. It can be seen that application of a magnesium Mg$^{++}$ signal does not induce any PRP coagulating effect.

Thus, the biological control system constituted by plasma rich in platelets makes it possible to verify that the characteristic signal of calcium Ca$^{++}$ has a coagulating effect.

Thus, the sensitive biological system constituted by plasma rich in platelets makes it possible to test whether a characteristic signal has a coagulating effect.

Protocol No. 2. "In Vivo" Experiment; Coagulating or Anticoagulant Action of Characteristic Electric Signals This protocol has the aim of demonstrating that:
on the one hand, the method and system described make it possible
to produce a characteristic electric signal for the Ca$^{++}$ ion and for heparin, and
to apply this electric signal to a receptor substance presenting after treatment respectively a coagulating or anticoagulant effect.
on the other hand, the method and system described make it possible to test a substance having respectively a coagulating or anticoagulant effect.

As biological control system making it possible to reveal the coagulating or anticoagulant effect of the treated substance, or as sensitive biological system making it possible to test the coagulating or anticoagulant effect of a substance, one uses a rabbit which is administered, under the tongue, with water treated by means of a characteristic electric signal from the source substance.

The water used is water for injectable preparation from Biosédra in 10 ml ampoules.

1. The water (10 ml) is placed in a tube 50 at the centre of an electromagnetic bobbin 51. The water is exposed to the characteristic signal under consideration for 10 minutes with a voltage at the bobbin terminals of 10 V.
2. The water is then shaken for 15 seconds at the maximum speed of the vortex.
3. The rabbit is then administered under the tongue with 1 ml of the water thus treated by the characteristic signal under consideration.

Blood samples (1 ml) are taken in glass tubes from the ear artery, before administration, and then 1, 5, 10, 15 and 30 minutes after administration of the treated water.

The results obtained are presented in the table below:

| | Coagulation evaluation | |
|---|---|---|
| Sampling time | Heparin Signal Av. ± 1SD(n) | Heparin + Protamine Complex Signal Av. ± 1SD(n) |
| before administration | 2.0 ± 0.0(3) | 2.0 ± 0.0(3) |
| 1 min. | 0.0 ± 0.0(6) | 2.0 ± 0.0(6) |
| 5 min. | 1.33 ± 1.03(6) | 2.0 ± 0.0(6) |
| 10 min. | 1.33 ± 1.03(6) | 2.0 ± 0.0(6) |
| 15 min. | 1.42 ± 0.97(7) | 2.0 ± 0.0(6) |
| 30 min. | 2.00 ± 0.00(7) | 2.0 ± 0.0(6) |

Interpretation

It can be seen that administration of water treated by the characteristic signal of heparin has an inhibiting effect on blood coagulation for fifteen minutes. On the other hand, water treated by the signal of the heparin+protamine complex produces no inhibiting effect.

Thus, the biological control system constituted by an animal makes it possible to verify whether a receptor substance treated by the characteristic signal of heparin, particularly water, has an anticoagulant effect.

Thus, the sensitive biological system constituted by an animal makes it possible to test, by controlling the characteristic signal of a substance (for example the heparin+protamine complex), whether this substance has a coagulating or anticoagulant effect.

It is thus established that one can control the production of homeopathic products by the utilisation of substances with a known effect (such as heparin) and by checking that the homeopathic products (granules, solutions, etc.) produced from this substance also have, themselves, at the end of the chain, the corresponding activity (in the example described, that of anticoagulant).

The characteristic signal of a drug or a receptor substance treated by the characteristic signal of a drug has the same biological effects as the drug which is the source of the signal under consideration.

In the same way, similar anticoagulant effects on rabbit or human blood or plasma are obtained with hirudin. The signals coming from hirudin show a greater anticoagulant effect than those coming from heparin.

The results obtained with hirudin and rabbit blood are given below:

| | Coagulation evaluation after 20 min. | |
|---|---|---|
| Concentration in Ca$^{2+}$ (mM) | Hirudin Signal working data | Water Signal working data |
| 1 | | |
| 2 | 0.0 | 0.0 |
| 3 | 0.0 | 2.2 |
| 4 | 0.1 | 2.2 |

The results obtained with hirudin and human blood are given below:

| | Coagulation evaluation Ca$^{2+}$: 7.5 mM | |
|---|---|---|
| Time (min.) | Hirudin Signal working data | Water Signal working data |
| 10 | 0.0 | 0.0 |
| 20 | 0.0 | 1.2 |
| 30 | 1.1 | 2.2 |
| 40 | 2.2 | 2.2 |

-continued

| | Coagulation evaluation $Ca^{2+}$: 7.5 mM | |
|---|---|---|
| Time (min.) | Hirudin Signal working data | Water Signal working data |
| 50 | 2.2 | 2.2 |
| 1 hr | 2.2 | 2.2 |

Method and Protocol: "Coagulation In Vitro"

Coagulation of plasma is slowed down when it has been mixed with water which has previously been exposed to the heparin electromagnetic signal. Heparin is recorded at a molecular concentration.

Water comprising calcium ion (Ca2+) is exposed to a digitally-recorded heparin (or water as control) signal. Then, Water-Ca2+ is mixed with decalcified plasma and putted into a 96 well plate. Coagulation is measured with a spectrophotometer and is expressed in Optical Density.

A delay or an inhibition of the coagulation of the plasma by the calcium by the heparin electromagnetic signal is observed.

Method for Producing Characteristic Electric Signal

The method according to the invention for producing characteristic electric signal delivers exploitable signal from an active substance, heparin for instance, as an anticoagulant which inhibits the prothrombin/thrombin phase of coagualation.

Distilled water (DW) have previously been submitted to an applicator of characteristic electric signal coming from heparin. DW is set in an electromagnetic field radiated by a transducer, typically a bobbin with the following characteristics: bobbin with internal diameter 50 mm, length 80 mm, R=3.6 ohms, 3 layers of 112 turns of copper wire, field on the axis to the centre 44 Oe/A, and on the edge 25 Oe/A. Which distilled water "traited" are applied to the biological control system, in this case, plasma coagulation.

Variations of electromagnetic fields are captured by an electromagnetic coil. As an example of such a transducer, one can mention very sensitive small copper wire bobbins with an impedance of 300 Ohms; internal diameter of 6 mm, external diameter of 16 mm, length 6 mm, normally used as telephone receivers.

The characteristic electric signal available at the output from the transducer are amplified by a preamplifier. The amplifier-preamplifier has the following specifications: passband from 10 Hz to 20 kHz, gain 50 to 100 for an input sensitivity of +/−100 mV or gain 500 to 2000 for an input sensitivity of +/−5 mV.

These electric signals are subtracted by an opposition series connection to the signals derived from the first transducer. Thus one obtains signals more representative of the interaction between the specific excitation field and the substance. In the case of a second embodiment variant, the processing means take into account the characteristics of the specific excitation field and reprocess the characteristic electric signals in the following way. First of all one proceeds by calculating the spread of the power spectral density (PSD). Then this PSD is contracted by conserving only the frequency band ranging for example from 140 Hz to 14 kHz, and reconstituting a signal from this PSD and randomly generated phases, and finally calibrating the power of the signal thus produced.

This method tests the inhibition of plasma coagulation by heparin signal. During blood coagulation there is a complex series of molecular interactions. One of the molecules is thrombin. Thrombin is a serine proteinase that converts fibrinogen to fibrin. Heparin is an anticoagulant which inhibits the prothrombin/thrombin phase of coagulation. Calcium ion (Ca2+) is necessary to coagulation.

Rationale of the Test:

When Ca2+ is added to decalcified plasma, the latter undergo coagulation, which is prevented by heparin. Digitally-recorded heparin (or water as control) signal is "played" to water, which is added to decalcified plasma alongside with Ca2+.

The digital heparin signal significantly prolongs the coagulation. Bovine, Rabbit, sheep and human plasma have been demonstrated to be sensitive to the anticoagulant signal.

The invention claimed is:

1. A method comprising:
    contacting a composition comprising an isolated coagulating agent or an isolated anticoagulating agent with an electric field, a magnetic field, or an electromagnetic field;
    transforming the field to produce a signal by employing a transducer-receiver, the signal being characteristic of the isolated coagulating agent or isolated anticoagulating agent;
    applying the signal to a biological system devoid of the isolated coagulating agent or isolated anticoagulating agent by employing a transducer-transmitter;
    wherein, after applying, the biological system can cause or undergoes coagulation or anticoagulation.

2. The method of claim 1, wherein the coagulating agent is calcium ion.

3. The method of claim 1, wherein the anticoagulating agent is heparin.

4. The method of claim 1, wherein the biological system is blood or plasma.

5. The method of claim 1, wherein applying comprises applying the signal to a substance that can then be administered to a biological system.

6. The method of claim 5, wherein the substance is a homeopathic substance.

7. The method of claim 1, wherein the signal is an electric signal.

8. A method comprising:
    contacting a composition comprising calcium ion or heparin with an electric field, a magnetic field, or an electromagnetic field;
    transforming the field to produce a signal by employing a transducer-receiver, the signal being characteristic of calcium or heparin;
    applying the signal to a biological system devoid of calcium ion or heparin by employing a transducer-transmitter;
    wherein, after applying, the biological system can produce or undergo coagulation or anticoagulation.

* * * * *